United States Patent [19]

Kurchacova et al.

[11] Patent Number: 5,229,296

[45] Date of Patent: Jul. 20, 1993

[54] USE OF POLYMER-COPPER COMPLEX TO CONTROL INTERFERENCE OF BIOLOGICAL SUBSTANCES IN COLORIMETRIC TEST SYSTEMS

[75] Inventors: Elva Kurchacova, Boca Raton, Fla.; Meitak T. Yip, Elkhart, Ind.

[73] Assignee: Miles Inc., Elkhart, Ind.

[21] Appl. No.: 816,339

[22] Filed: Dec. 30, 1991

[51] Int. Cl.$^5$ ............................................. G01N 33/72
[52] U.S. Cl. ........................................ 436/66; 436/63; 436/74; 436/80; 436/97; 436/175; 436/177; 435/25; 435/28
[58] Field of Search ...................... 436/63, 66, 80, 95, 436/97, 74, 175, 177, 904; 435/25, 28

[56] References Cited

U.S. PATENT DOCUMENTS

| | | | |
|---|---|---|---|
| 4,303,408 | 12/1981 | Kim et al. | 436/97 X |
| 4,600,689 | 7/1986 | Matsui et al. | 435/25 |
| 4,892,816 | 1/1990 | Akiba et al. | 435/25 X |
| 5,057,435 | 10/1991 | Denney | 436/79 |
| 5,079,140 | 1/1992 | Albarella et al. | 435/25 X |

OTHER PUBLICATIONS

Andersson, L., et al., Cancer Res., 47(14), 3624–3626, Jul. 15, 1987 Facile Resolution of α-Fetoproteins and Serum Albumins by Immobilized Metal Affinity Chromatography.

Berk, P. D., et al., Appln. Immobilized Enzymes & Proteins, vol. 1, pp. 297–317; Removal of Bilirubin from Blood by Affinity-Competition Chromatography Over Albumin-Agarose Gel.

Primary Examiner—Jill A. Johnston
Assistant Examiner—Maureen M. Wallenhorst
Attorney, Agent, or Firm—Jerome L. Jeffers

[57] ABSTRACT

Disclosed is a method for separating biological substances, particularly hemoglobin or bilirubin, from blood plasma or serum which involves contacting the plasma or serum with a water insoluble complex of a polymer containing multiple pendant carboxyl groups and copper.

15 Claims, No Drawings

USE OF POLYMER-COPPER COMPLEX TO CONTROL INTERFERENCE OF BIOLOGICAL SUBSTANCES IN COLORIMETRIC TEST SYSTEMS

BACKGROUND OF THE INVENTION

There are available to the clinical analyst various test devices and methods for the rapid determination of certain constituents in blood samples which if found to be outside the range of a predetermined concentration indicate a potential pathological condition.

In the analysis of blood for analytes such as glucose, lactate, uric acid and ethanol it is common practice to first of all reduce the whole blood sample being tested to plasma by precipitating red blood cells or to blood serum by causing the blood to coagulate. In either case, in the absence of extreme care in preparing the sample, a portion of the red blood cells can be lysed thereby releasing biological impurities such as hemoglobin and bilirubin derived from hemoglobin into the blood sample.

In the analysis of the blood sample for a predetermined analyte, there is typically employed an oxidative reagent system in which an oxidase enzyme selected in accordance with a predetermined analyte such as glucose reacts with the analyte in the presence of oxygen to provide hydrogen peroxide which, in the presence of a peroxidative substance, will oxidize a suitable redox indicator to convert it to its oxidized, colored form and, by visually or instrumentally determining the intensity of the color one can quantitatively determine the concentration of analyte in the blood sample.

In addition to the oxidative system described above, the present invention can be used in combination with reductive system which is represented by the following equations in which glucose is the analyte of interest, ATP represents adenosine triphosphate, ADP represents adenosine diphosphate, AND represents nicotinamide-adenine dinucleotide, NADH represents the reduced form of AND, and NBT represents nitroblue tetrazolium:

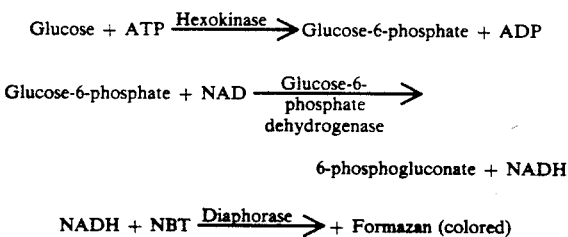

The intensity of the formazan color produced by this system is directly proportional to the glucose concentration in the system.

In order for such a test to have the required sensitivity, it is essential that the blood specimen being tested be as nearly colorless as is practical under the test conditions in order to avoid interference with the determination of the intensity of the color formed. Accordingly, lysis of the red blood cells and the consequent release of biological substances such as hemoglobin and bilirubin is problematical in the context of these colorimetric determinations due to their interference with the reading of the specimen's reflectance by spectrophotometric means.

In their article appearing in *Cancer Res.*, 47(14), 3624-6 (1987) Anderson et al report that human serum alpha-fetoprotein and albumin were chromatographed on immobilized iminodiacetic acid charged with either $Co^{+2}$, $Ni^{+2}$, $Cu^{+2}$ or $Zn^{+2}$. Both proteins were bound to $Cu^{+2}$ and were partially resolved by affinity elution with imidazole.

Berk et al report in *Biomed. Appln. Immobilized Enzymes & Proteins*, Vol. 1, Pp. 297-317 that bilirubin can be removed from blood by affinity-competition chromatography over an albumin-agarose gel.

It is an object of the present invention to provide a novel method for the removal of extraneous biological substances such as hemoglobin and/or bilirubin from samples of blood serum or plasma.

It is a further object to provide such a method which renders the blood sample more amenable to the colormetric analysis of various analytes contained therein.

SUMMARY OF THE INVENTION

The present invention is an improvement in the method of analyzing blood serum or plasma by a colorimetric test in which a redox indicator is reduced or oxidized by the use of an appropriate reagent system to provide a colored response to the analyte. The improvement involves contacting the blood sample with an insoluble copper complex of a polymeric material bearing multiple pendant carboxyl groups to form an insoluble reaction product with potentially interferring biological substances in the blood sample which can be removed therefrom by solid/liquid separatory techniques.

DESCRIPTION OF THE INVENTION

The present invention is directed to a method for the removal of colored interferants from blood serum or plasma. The method involves the ability of $Cu^{++}$ to complex with polymers containing multiple pendant carboxyl groups which complex in turn has the ability to form an insoluble combination with biological materials such as hemoglobin and bilirubin present in the blood sample thereby facilitating their removal therefrom.

The carboxylic group containing polymers useful in the present invention are generally water soluble in their uncomplexed state, however, when they are converted to their copper complex the resultant is essentially insoluble in water. Suitable carboxylic group polymers include those polymers which are capable of forming water insoluble complexes with copper-ions when they are contacted in aqueous solution with a soluble copper salt, e.g. cupric sulfate. The carboxyl group density, i.e. ratio of carboxyl groups to the number of carbon atoms in the polymer backbone, is not critical and will typically be within the range of from 1:9 to 9:1 and preferably within the range of from 1:3 to 3:1. Ideally, this ratio will be about 1:1 which provides the best combination of solubility characteristics and affinity for the potentially interferring biological materials upon its conversion to the copper complex. Accordingly, suitable polymers can be selected from polymers of the general formula:

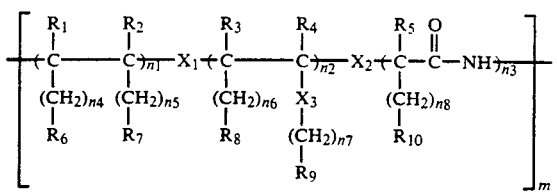

where
$n_1 = 0$ to 3
$n_2 = 0$ to 3
$n_3 = 0$ to 3, provided that at least 1 of $n_1$, $n_2$ or $n_3$ is not 0;
$n_4$, $n_5$, $n_6$, $n_7$ and $n_8 = 0$ to 6;
$R_1$, $R_2$, $R_3$, $R_4$ and $R_5$ are H, OH, alkoxy containing from 1 to 4 carbon atoms,

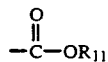

or $-NHR_{11}$ where $R_{11}$ is lower alkyl of 1 to 6 carbon atoms.

$R_6$, $R_7$, $R_8$, $R_9$ and $R_{10}$ are H, carboxyl, OH, sulfonic acid, imidazolyl or pyridyl, provided that at least 1 of $R_6$, $R_7$, $R_8$, $R_9$ and $R_{10}$, and preferably 2 or 3 of these moieties represent carboxyl groups, and $X_1$, $X_2$, $X_3$ are a single bond, $-O-$,

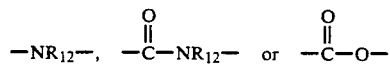

where $R_{12}$ is H or lower alkyl of 1 to 6 carbon atoms.

The degree of polymerization, i.e. value of m in the above formula, is not critical provided that it is within a range that forms a polymer copper complex when contacted with copper ions in aqueous solution. Typically, the degree of polymerization will be from about 10 to about 600 with a degree of polymerization of from about 40 to about 130 being preferred.

The sulfonic acid, imidazolyl and pyridyl groups, when present, enhance the solubility characteristics of the polymer in aqueous solution before its complexation with copper. Such enhanced solubility may be necessary when a polymer having a carboxyl group density towards the low end of the density ranges mentioned above is used to prepare the complex. In addition, carboxylic derivative polymers such as maleic anhydride/styrene copolymers can be used provided that they provide the requisite ratio of carboxylate to carbon atoms in the polymer backbone.

More specifically, preferred polymers include:

polyacrylic acid 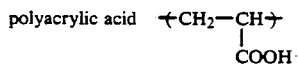 (1)

polyaspartic acid 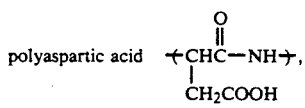 (2)

and polyglutamic acid 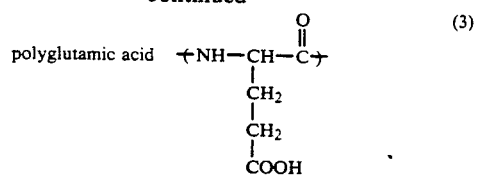 (3)

The most preferred polycarboxylic polymer is the hydrolyzed form of Gantrez®, poly(methylvinyl ether/maleic acid) which is manufactured by the GAF Corporation,

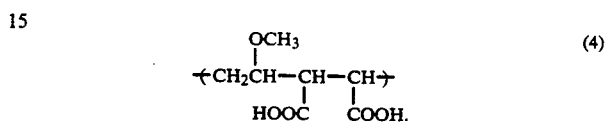 (4)

The carboxylic acid polymer is complexed with copper by contacting it in aqueous solution with a suitable source of copper ion, e.g. copper sulfate. In this procedure the polymer/copper complex precipitates from the aqueous medium and is recovered by filtration or similar means.

The soluble polymer bearing multiple carboxyl groups is rendered essentially insoluble in water upon being complexed with copper which makes it an ideal candidate for scavenging biological materials from blood serum or plasma because the combination of polymer-copper complex/biological material can be readily separated from serum or plasma by standard solid/liquid separatory techniques such as centrifugation with decantation or by filtration. In a preferred method of practicing the present invention the polymer-copper complex is ingrained in a filter means, such as filter paper, and the serum or plasma is passed through the filter paper wherein the biological materials, particularly hemoglobin and bilirubin, adhere to the filter bound complex and are effectively removed from the blood sample. An alternative procedure in which the complex is added directly to the blood sample also works well. In this embodiment, the insoluble reaction product of the polymer-copper complex and biological material can be separated from the blood sample by centrifugation with decantation or by filtration.

Typically, the polymer-copper complex will be combined with the blood sample in an amount of from about 0.2 to about 20% w/v with the preferred amount being from about 0.5% to about 10%. This concentration will vary, of course, depending on the amount of biological material to be scavenged and the concentration of carboxyl groups on the polymer backbone which are capable of being derivatized with copper. The preferred copper complex, prepared using Gantrez®, will normally be combined with the blood serum or plasma in an amount of from about 0.7 to about 7% w/v in order to achieve the desired level of purification.

While we do not wish to be bound by any particular theory of how our invention operates, it is believed that hemoglobin and bilirubin are bound by interaction of their carboxylic acid and/or amino groups with the previously described polymer/copper complex.

The method of practicing the present invention is further illustrated by the following examples:

EXAMPLE 1

A Gantrez® acid/Cu++ complex was prepared as follows:

About 1.7 g (0.1M) of Gantrez® S-95 100 ml of deionized water until it was completely dissolved. Gantrez® S-95 is the hydrolyzed form of Gantrez®, poly(methyl vinyl ether/maleic anhydride). Next a solution of cupric sulfate (0.1M) was added to the Gantrez® acid solution slowly with vigorous stirring. After mixing for 30 minutes a blue precipitate separated out of the solution. This precipitate was collected by filtration and washed with deionized water thoroughly until the filtrate was colorless in order to remove all of the unbound cupric ion. This solid was dried to provide a blue Gantrez® acid copper complex.

The effectiveness of this complex in a liquid assay and in the solid phase to cause hemoglobin and bilirubin separation was determined by obtaining test results using both a liquid and filter paper format and comparing these test results with those obtained using the same formats without the complex.

Liquid Assay-Hemoglobin

Six test tubes containing 0, 10, 20, 30, 50 and 70 mg of the Gantrez® acid-copper complex were mixed with 780 μg hemoglobin and distilled water up to 1.3 mL. Each tube was shaken for one minute and then centrifuged. The supernatant solution was separated and an absorbance measurement was made using a Beckman spectrophotometer at 560 nm (the wavelength of maximum absorbance for hemoglobin). A blank sample containing no complex was used as control. The results of this experiment are set out in Table I.

TABLE I

| Complex | ABS at 560 nm | % Reduction |
|---|---|---|
| None | 0.2929 | — |
| 10 mg | 0.1680 | 43.00 |
| 20 mg | 0.1377 | 53.00 |
| 30 mg | 0.1282 | 56.00 |
| 50 mg | 0.0891 | 69.59 |
| 70 mg | 0.0640 | 78.50 |

Liquid Assay-Bilirubin

Serum test tubes containing 0, 10, 22.8, 35.7, 6.5, 60.8, 71.8 and 84 mg Gantrez® acid-copper complex were mixed with 10 μg of conjugated bilirubin and distilled water up to 1.3 mL. Each tube was shaken for one minute and centrifuged. The supernatant solution was separated and an absorbance measurement was taken at 456 nm. The control sample contained bilirubin without any addition of the complex. The results of this experiment are set out in Table II.

TABLE II

| Complex | ABS at 456 nm | % Reduction |
|---|---|---|
| Control | 0.6198 | — |
| 10 mg | 0.3336 | 46.00 |
| 22.8 mg | 0.3491 | 44.00 |
| 35.7 mg | 0.3502 | 44.00 |
| 46.5 mg | 0.3087 | 50.00 |
| 60.8 mg | 0.2978 | 52.00 |
| 71.8 mg | 0.2967 | 52.00 |
| 84.0 mg | 0.2287 | 55.00 |

From Tables I and II it can be determined that the polymer/Cu complex is effective in removing both hemoglobin and bilirubin from aqueous media.

EXAMPLE 2

In this experiment a Gantrez®-Acid copper complex was applied to an absorbant carrier matrix, i.e. filter paper. A piece of filter paper was first impregnated from its 0.25M solution of Gantrez® Acid. After drying at 50° C. for 10 minutes, the matrix was impregnated with a second solution containing 0.125M cupric sulfate and again dried at 50° C. for 10 minutes. The complex treated matrix was cut into 0.2×0.2 inch wide ribbons and arranged in a two-layer stacked format to provide a reagent pad. The matrix Gantrez®-Acid copper complex was contacted with aqueous hemoglobin at various concentrations by pipetting the hemoglobin solution onto the upper layer of the test pad.

The results of this experiment are set out in Table III.

TABLE III

| Hemoglobin Conc. mg/dL | K/S Hemoglobin Samples | K/S Hemoglobin + Complex | % Reduction |
|---|---|---|---|
| 0 | 0.0753 | 0.0753 | — |
| 10 | 0.1117 | 0.0812 | 84.00 |
| 250 | 0.1485 | 0.0861 | 85.25 |
| 500 | 0.2529 | 0.1380 | 64.70 |
| 1000 | 0.4153 | 0.2639 | 44.53 |
| 2000 | 0.7826 | 0.6546 | 18.10 | where K/S value was determined from the equation:

$$K/S = \frac{(1-R)^2}{2R}$$

to transform the reflectance data (R) to a function (K/S) that is proportional to the chromophore concentration.

For purposes of this example, the lower pad contained no reagent so that the reflectance values represent only the amount of hemoglobin which penetrated the first upper pad and entered the lower pad. In practice, the lower pad would be impregnated with a reagent/enzyme system of the type previously described to provide a color change when contacted with a predetermined analyte in the blood sample. The data of Table III demonstrate that the interference of hemoglobin with the colorimetric determination of the analyte is greatly diminished by using the system of the present invention.

This experiment illustrates how a stacked device for the one step colormetric analysis for various analytes can be prepared. Such a device would comprise a reagent layer having a filter layer of absorbant material impregnated with the polymer-copper complex located above it through which the blood serum or plasma passes. This stacked system, which may optionally have a filter layer on top of the complex containing layer for removing red blood cells, may be affixed to a transparent support such as a clear polyester strip through which the reaction of the blood with components in the reagent layer can be viewed with reduced interference from hemoglobin or bilirubin which has been effectively removed from the blood sample before it reaches the reagent layer.

What is claimed is:

1. In the method of analyzing a sample of blood serum or plasma by a colorimetric test in which a redox indicator is reduced or oxidized to provide a colored product wherein the intensity of such colored product is proportional to the concentration of a predetermined analyte, the improvement which comprises contacting the sample of blood serum or plasma with a water insoluble complex prepared from copper and a polymer containing multiple pendant carboxyl groups, which complex selectively combines with hemoglobin and bilirubin in the sample to render these substances insoluble in the sample, and separating the insolubilized hemoglobin and bilirubin from the blood serum or plasma sample.

2. The method of claim 1 wherein the polymer is characterized by the formula:

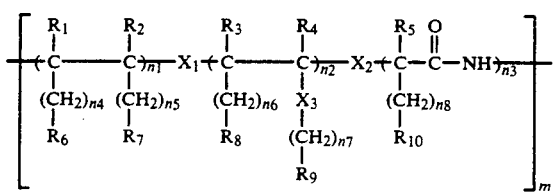

where
$n_1 = 0$ to 3
$n_2 = 0$ to 3
$n_3 = 0$ to 3, provided that at least 1 of $n_1$, $n_2$ or $n_3$ is not 0;
$n_4$, $n_5$, $n_6$, $n_7$ and $n_8$ independently $= 0$ to 6;
$X_1$, $X_2$ and $X_3$ represent a single bond, $-O-$, $NR_{12}$, $C-NR_{12}$ or

where $R_{12}$ is H or lower alkyl of 1 to 6 carbon atoms;

$R_1$, $R_2$, $R_3$, $R_4$ and $R_5$ are independently H, OH, alkoxy of 1 to 4 carbon atoms,

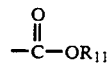

or $-NHR_{11}$ where $R_{11}$ is lower alkyl of 1 to 6 carbon atoms and $R_6$, $R_7$, $R_8$, $R_9$ and $R_{10}$ are independently H, carboxyl, OH, sulfonic acid, imidazolyl or pyridyl;

provided that at least 1 of $R_6$, $R_7$, $R_8$, $R_9$ and $R_{10}$ is a carboxyl group and m is the degree of polymerization.

3. The method of claim 2 wherein two or more of $R_6$, $R_7$, $R_8$, $R_9$ or $R_{10}$ represent carboxyl.

4. The method of claim 3 wherein the ratio of carboxyl groups to the number of carbon atoms in the polymer backbone is in the range of 1:9 to 9:1.

5. The method of claim 4 wherein the ratio is in the range of 1:3 to about 3:1.

6. The method of claim 5 wherein the ratio is about 1:1.

7. The method of claim 2 wherein m can range from about 10 to about 600.

8. The method of claim 7 wherein m can range from about 40 to about 130.

9. The method of claim 1 wherein the polymer is polyacrylic acid, polyaspartic acid, polyglutamic acid or poly(methylvinyl ether/maleic acid).

10. The method of claim 9 wherein the polymer is hydrolyzed poly(methylvinyl ether/maleic acid).

11. The method of claim 1 wherein the complex is present in an amount of from about 0.2 to about 20% w/v of the blood sample.

12. The method of claim 11 wherein the complex is present in an amount of from about 0.5 to about 10% w/v.

13. The method of claim 1 wherein the polymer is hydrolyzed poly(methylvinyl ether/maleic acid) and its copper complex is present in an amount of from about 0.7 to about 10% w/v of the blood sample.

14. The method of claim 1 wherein the water insoluble complex of copper and the polymer is ingrained in a filter means and the blood serum or plasma sample is passed through such filter means.

15. The method of claim 14 wherein the filter means is filter paper.

* * * * *